United States Patent
Hartholt et al.

(10) Patent No.: US 11,540,732 B2
(45) Date of Patent: Jan. 3, 2023

(54) DUAL PRESSURE SENSOR AORTIC-VALVE CATHETER

(71) Applicant: Wellinq Medical B.V., Leek (NL)

(72) Inventors: Hendrik Hartholt, Oosterwolde (NL); Ronald Arthur van den Broek, Pijnacker (NL)

(73) Assignee: Welling Medical B.V., Leek (NL)

( * ) Notice: Subject to any disclaimer, the term of this patent is extended or adjusted under 35 U.S.C. 154(b) by 212 days.

(21) Appl. No.: 16/281,314

(22) Filed: Feb. 21, 2019

(65) Prior Publication Data

US 2019/0254543 A1    Aug. 22, 2019

Related U.S. Application Data

(60) Provisional application No. 62/633,944, filed on Feb. 22, 2018.

(51) Int. Cl.
*A61B 5/0215* (2006.01)
*A61B 5/00* (2006.01)

(52) U.S. Cl.
CPC ........ *A61B 5/02158* (2013.01); *A61B 5/6853* (2013.01); *A61B 5/6855* (2013.01);
(Continued)

(58) Field of Classification Search
CPC .............. A61B 5/02158; A61B 5/6855; A61B 5/6853; A61B 5/6857; A61B 5/042; A61B 5/0285; A61B 2562/043; A61B 2562/0247

See application file for complete search history.

(56) References Cited

U.S. PATENT DOCUMENTS

| 3,794,026 A | * | 2/1974 | Jacobs | A61M 25/04 128/207.15 |
| 9,332,914 B2 | * | 5/2016 | Langston | A61B 5/6857 |

(Continued)

FOREIGN PATENT DOCUMENTS

| WO | WO-2008126074 A2 | * | 10/2008 | ......... A61B 5/02152 |
| WO | WO-2010027957 A2 | * | 3/2010 | ......... A61B 5/02055 |
| WO | WO-2017156039 A1 | * | 9/2017 | ........... A61B 5/6859 |

OTHER PUBLICATIONS

Sharma T, Aroom K, Naik S, Gill B, Zhang JX. Flexible thin-film PVDF-TrFE based pressure sensor for smart catheter applications. Ann Biomed Eng. Apr. 2013;41(4):744-51. doi: 10.1007/s10439-012-0708-z. Epub Dec. 1, 2012. PMID: 23519532. (Year: 2013).*

(Continued)

*Primary Examiner* — Sean P Dougherty
*Assistant Examiner* — Alexander H Connor
(74) *Attorney, Agent, or Firm* — The Webb Law Firm (57) ABSTRACT

Disclosed is a system and method for in-situ and instantaneous measurement of a pressure gradient by real-time localized pressure measurement with two or more pressure sensors, operating with respect to blood pressure gradient across the aortic valve, or other heart valves, and associated regurgitation of blood flow due to leakage resulting from insufficient valve closure. The system includes a multi-sensor catheter, with sensors arranged along the length of the distal segment of the catheter body, spaced apart to provide simultaneous pressure measurement on either side of the valves of the heart, in addition to one or more lumina in the core of the catheter that will provide a path for introduction of diagnostic fluids which flow out through a multitude of holes in the body of the distal segment of the catheter body.

18 Claims, 5 Drawing Sheets

(52) U.S. Cl.
CPC .... *A61B 5/6857* (2013.01); *A61B 2562/0247* (2013.01); *A61B 2562/043* (2013.01)

(56) References Cited

U.S. PATENT DOCUMENTS

| | | | | |
|---|---|---|---|---|
| 2011/0144637 A1* | 6/2011 | Pageard | ............... | A61B 5/6869 606/41 |
| 2013/0255390 A1* | 10/2013 | Riley | ................... | G01L 11/025 73/705 |
| 2015/0025330 A1* | 1/2015 | Davies | .................. | A61B 5/743 600/301 |
| 2017/0027458 A1* | 2/2017 | Glover | .................. | G16H 20/40 |
| 2017/0119260 A1* | 5/2017 | Gilbert | ................. | A61M 5/007 |
| 2019/0290139 A1* | 9/2019 | Sio | ..................... | A61B 5/02125 |

OTHER PUBLICATIONS

Sven Poeggel, "Optical Fibre Pressure Sensors in Medical Applications", Sensors 2015, 15, 17115-17148, Published: Jul. 15, 2015 (Year: 2015).*

Sharma T, Aroom K, Naik S, Gill B, Zhang JX. Flexible thin-film PVDF-TrFE based pressure sensor for smart catheter applications. Ann Biomed Eng. Apr. 2013;41(4):744-51. doi: 10.1007/s10439-012-0708-z. Epub Dec. 1, 2012. PMID: 23519532. (Year: 2013) (Year: 2013).*

* cited by examiner

DUAL PRESSURE SENSOR AORTIC-VALVE CATHETER

CROSS-REFERENCE TO RELATED APPLICATION

This application claims the benefit of U.S. Provisional Patent Application No. 62/633,944 filed Feb. 22, 2018, the disclosure of which is hereby incorporated by reference in its entirety.

FIELD

The present invention falls in the field of cardiac catheters, more specifically the field of minimally invasive diagnostic systems with respect to cardiac valve stenosis, next to vascular stenosis.

BACKGROUND

Aortic regurgitation is one of the consequences of aortic stenosis, in which, due to a pathological condition, the aortic valve becomes calcified, with associated stenosis, and as a result the valve will not open normally. The opening and closing of the aortic three-leaflet valve coincides with the contraction of the left ventricle, pushing blood out of the ventricle during systole, followed by relaxation of the heart muscle, causing the aortic valve to close due to the pressure resulting from the blood in the vascular system on the distal side of the valve, which is subject to compliance. The aortic compliance will make the aorta swell over a certain length during filling under the systolic ejection from the left ventricle. This swelling will subside, and the aortic diameter will return to the smaller diameter once the fill pressure has been removed during the diastolic event of the heartbeat. The left ventricular outflow of blood contains oxygen rich blood, which flows through the aorta into the main body, as well as supplying the heart itself with oxygen through the coronary vessels. Due to the calcification of the leaflets of the tricuspid valve, connecting the left ventricle to the aorta, the imperfect closure of the valve will result in regurgitation of the blood-flow, reverting back into the left ventricle during diastole. The regurgitation resulting from the partial closure of the stenotic aortic valve hence causes insufficiency in oxygen rich blood to flow into the main circulation as well as diminishes the oxygen supply to the heart muscle itself.

Aortic valve stenosis is a pathological condition that may result from rheumatic fever during childhood, or age-related calcification, starting for a select group of patients in their late 40's, progressively worsening with increasing age, culminating to debilitating conditions of degenerative aortic stenosis when the age is older than 70 for the general male population. The prevalence of assorted types valve disease is influenced by gender. On average, the frequency of degenerative valve disease is relatively similar for both sexes. On the other hand, the occurrence of rheumatic mitral stenosis is relatively common in women. A small number of gender based differences in the physiopathology of degenerative aortic stenosis are recognized. Generally, the extent of calcification is greater in men than in women. Furthermore, a woman's ventricle, on average, responds to comparable reductions in valve area with an increased slope in gradient and concurrently greater contractility. Based on prognosis, the mortality associated with heart surgery is generally higher in women than for men. The latter applies to both valve surgery as well as coronary artery surgery. Pregnancy presents actual greater complications for women with valvular heart disease. Women with significant valve lesions considering pregnancy are often advised to the have the valve stenosis correct pre-emptively. When considering treatment of aortic valve disease in pregnant women with anticoagulants, specifically during the first trimester, there will be the potential for increased risks of prosthetic valve thrombosis, next to fatal embryopathy.

Valvular insufficiency describes the condition when a closed cardiovascular valve is not hermetically sealed. Under these conditions blood will flow backwards into the cardiac chamber, which is proximal from the outflow valve, constituting regurgitation.

Associated with regurgitation are turbulent flow streams, which will generate audible noise under examination by means of a stethoscope, which has a clinical diagnosis as heart murmurs.

Due to the regurgitation the diastolic pressure in the aorta will become lower than for a fully sealed closure under the condition of a healthy aortic valve.

Due to the aortic regurgitation the left ventricle will be filled from two sources, the other source being the left atrium of the heart. This combined fill process results in an increase in left ventricular volume. Based on the Frank Starling mechanism, this increase in end-diastolic volume will result in inotropic changes in the cardiac muscle contraction during the systolic events, hence elevating the aortic systolic pressure as well as increasing the left ventricular pressure, each at a different rate over the time of each heartbeat.

In some cases, genetic predisposition forms a major factor, specifically: the aortic valve can be composed of only two leaflets instead of three.

Various conditions of outflow constraints, including, but not limited to the valvular insufficiency due to for instance calcification of the valve, and associated stenosis, and the genetic fused bi-leaflet aortic valve condition result in flow impairment affecting the flow bed directly supplying the cardiac muscle, next to the main circulation. This reduction in flow has as an inherent drawback the reduction in the supply of dissolved essential constituents in the blood flow itself.

The diminished oxygen supply to the heart muscle tends to induce hypertrophy, in addition to the increased requirement in effort for forced expulsion of the blood in the vital volume, resulting in an enlargement of the heart muscle.

The hypertrophy and cardiac enlargement form a recursive mechanism, leading to a gradual weakening of the heart muscle with continuous enlargement. The compounding effects of muscle weakening and dilation result in further loss of aortic flow, with encompassing reduction in oxygen supply to the body and the heart muscle itself. Patients suffering from aortic stenosis and aortic valve calcification frequently become subject to angina, next to syncope, resulting from the deteriorated blood supply to the brain.

SUMMARY OF THE INVENTION

According to the present invention a solution to the debilitating conditions resulting from a stenotic aortic valve is the transcatheter placement of a replacement prosthetic aortic heart valve. In order to gauge the severity of the progress of aortic stenosis, a pressure gradient assessment across the aortic valve is performed, measuring the in-situ blood-pressure difference between the left ventricular pouch and the volume in the aortic arch. Based on the measured hemodynamic conditions an informed decision can be formed with respect to a prognosis for the treatment of the valve condition.

In particular, the invention can be used to measure the pressure profile associated with the time lapse of the aortic filling and the aortic-left-ventricular regurgitation.

The invention can also be used to measure the evolution of the increase of the aortic pulse-pressure (i.e. diastolic pressure subtracted from the systolic pressure for each cardiac contraction). This pressure profile will furthermore result in back-flow of blood into the pulmonary veins with associated increase in pulmonary capillary wedge pressure, and can potentially lead to pulmonary congestion, with pathological formation of edema.

This differential pressure measurement can be made in a preferential technique of individual respective pressure sensors placed both in the left ventricle and the aortic arch. For example, these pressure sensors can be placed on the exterior surface of a five French or six French size catheter, located at positions as such that the distance between the sensors provides stable pressure recording at both locations when the distal sensor location is placed through the aortic valve, in the left ventricle.

One presently preferential configuration would be a pigtail design, which is known in the art. The pigtail catheter has a distal spiral portion, or coil, extending above or below three hundred and sixty degrees. Another preferred embodiment will encompass a J-shape, or any variety of shapes combinations; spanning a curved extrusion lumen with or without a straight distal segment, curvature ranging between ninety and six hundred degrees. The extrusion tube may have one, two, three or more lumina. The distal tip design presents a conforming resilient, blunt smooth end, which reduces the risk for tissue damage when in tissue contact.

In addition to advancing the catheter over a guidewire to the location of interest, the catheter can provide a conduit for the delivery of contrast fluid while exposing the patient to x-ray radiation under fluoroscopic imaging while examining the full range of pathological conditions contributing to the patient discomfort or clinical problems.

The availability of a flexible catheter comprising two pressure sensors at a minimum separation to provide reliable, accurate and high spatial and temporal resolution pressure information with respect to two locations, proximal and respectively distal to a stenosis, while conforming to a guidewire, would benefit the clinician in minimally invasive diagnostic interrogation of stenosis present in the circulatory system.

In an embodiment of the invention, the catheter has multiple pressure sensor elements on the exterior wall of the shaft according to embodiments of the invention. The pressure sensors are placed in locations that will provide the means of placing one pressure sensor distal from a stenosis and a second pressure sensor proximal from a stenosis in a vascular lumen, respectively proximal and distal from a valve in the outflow orifice of the heart. More specifically, the invention describes the use of cardiac catheters in the use of performing procedures for the assessing the severity of aortic stenosis, in particular related to the calcification effects of the cardiac valves and associated reduction in the closure, and sealing, efficacy of these valves. The pressure sensors may be constructed of various materials, each with their specific associated mechanism-of-action for the conversion of a local pressure value into an electronic signal magnitude that is representative of the magnitude of the local in-situ pressure. The pressure sensor may be connected to the distal end of the laser catheter and may comprise any of various capacitive, resistive or piezoelectric materials. The mechanism of action for conversion of pressure into electronic signal, either analogue or digital, may comprise of any of the following materials, methods or sensor configurations, piezo-resistive [e.g. ceramic (PZT); single-crystal materials (e.g. quarts); polymer, such as Polyvinylidene Difluoride (PVDF); and respectively semiconductor based], capacitive, strain/potentiometric, thermal, ionizing, acoustic/resonant, electromagnetic, MEMS, fiber-optic, fluid-column (macroscopic) and various combinations of the aforementioned.

The system and means disclosed by this invention provide an accurate and high-resolution time-resolved as well as spatially resolved acquisition of multiple in-situ blood pressure measurements in a patient's vascular and cardiac system. The recorded pulsatile and transient pressure patterns for the various simultaneously recorded pressure values can be processed and displayed by an external monitoring system to provide the tools for a physician to make an informed decision about the pathological conditions of the cardiac valves of a patient and the advisable prognostic therapeutic path, or the vascular pathology with respect to the local lumen in which the pressure sensors are placed. The dual sensor catheter for diagnostic testing of the aortic stenosis conditions addresses the above problems. The invention preferably uses a braided construction to support the injection of contrast media under high pressure for high flow-rate instantaneous filling of the aortic sinuses of Valsalva, either flowing into the left ventricle when a stenosis is present (i.e. regurgitation) or not when the valve is clinically sealed, purposely within one heart-cycle. The catheter preferably contains a manifold for attachment of junctions that allow the attachment of a buffered saline solution injection, a guidewire transport, the high-pressure injection of a contrast medium, as well as the exchange over the guidewire with therapeutic devices. The high-pressure injection is furthermore facilitated by means of side holes in the distal portion of the catheter. The side holes may be arranged in a linear, spiral, alternating or random pattern around the surface of the catheter along a predefined segment length to endorse the atraumatic and non-damaging administration of high flow liquids under high pressure back-load.

The clinical value of this catheter design according to an embodiment of the present invention is the real-time assessment of leakage and regurgitation resulting from diseased and malfunctioning aortic valve anatomy. Another application is to verify that a new heart valve is placed correctly, the leakage of blood-flow from the left-ventricle into the aorta to be precise, alternatively the regurgitation through the aortic valve into the left ventricle. In clinical diagnostics the regurgitation can be ranked and classified and subsequently evaluated for potential treatment options. The catheter is generally placed under visual aid from fluoroscopy. Injection of contrast fluid through the core lumen of the catheter can provide a visual aid in the diagnostic process, which requires that the mechanical integrity of the catheter must be able to withstand high-pressure contrast, while the pressure measurement may continue real-time, respectively with minimum requirement that the pressure registration shall not be affected under the influence of the high-pressure contrast fluid injection (applied flow-pressure for contrast injection on the proximal end of the catheter, in excess of: 1200 PSI inlet pressure at the proximal end of the catheter). X-ray imaging is an integral part of the diagnostic process.

Additional clinical applications may be in the assessment of the degree of stenosis in locations in the lumen of the circulatory system itself.

Preferably, embodiments according to the present invention provide a catheter that has a wall that is resilient tot the high-pressure contrast injection. Also, it is prevented that flow of contrast changes the catheter dimensions, neither in diameter nor in length. Furthermore, it is prevented that the flow of contrast under high pressure injection damages the pressure chips function, both in accuracy and in stability (e.g. drift). The structural integrity of the catheter design ensures the continuous real-time acquisition of pressure recordings, simultaneously and synchronized in both the ventricle and the aorta.

The system according to a presently preferred embodiment provides the ability to perform simultaneously and synchronized pressure measurement in at least two locations, in addition to measurement while contrast fluid is injected under high pressure are an integral part of the design.

The main difference with currently available catheters is that these rely on the transfer of pressure from the location inside the left-ventricle, respectively the aorta by means of a fluid column to a pressure sensor located outside the body, for instance mounted on a pole standing next to the patient's bed, or another location with its own inherent pressure value inherent to the difference in height with respect to sea-level in reference to the sensor located in the bloodstream. The pressure transfer by means of a fluid column may have dampening due to momentum transfer as well as loss in frequency spectrum content resulting from wave-mechanical filtering.

BRIEF DESCRIPTION OF THE DRAWINGS

Exemplary embodiments of a lifting system and/or the method according to the present invention are described here below on the basis of a non-limitative exemplary embodiment therefor shown in the accompanying drawings, wherein.

DETAILED DESCRIPTION

The following description is merely exemplary in nature and is in no way intended to limit the invention, its application, or uses. While the disclosure is described as having exemplary attributes and applications, the present disclosure can be further modified. This application is therefore intended to cover any variations, uses, or adaptations of the disclosure using its general principles. Further, this application is intended to cover such departures from the present disclosure as come within known or customary practice of those skilled in the art to which this disclosure pertains and which fall within the limits of the appended claims. Accordingly, the following description of certain embodiments and examples should be considered merely exemplary and not in any way limiting.

Figure 1:
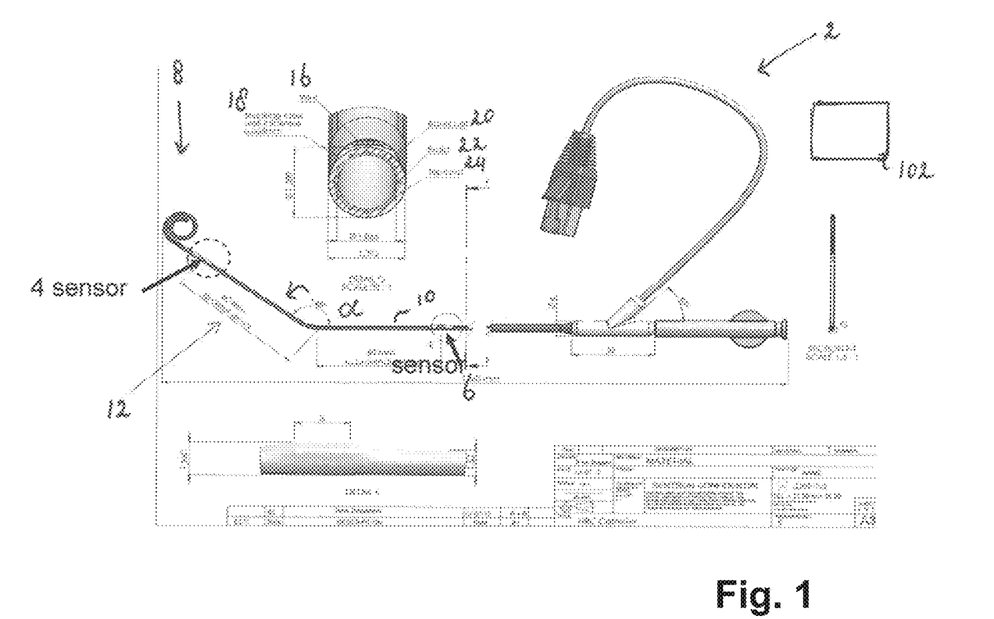
FIG. 1 shows an embodiment of a catheter according to the invention.
Figure 2:
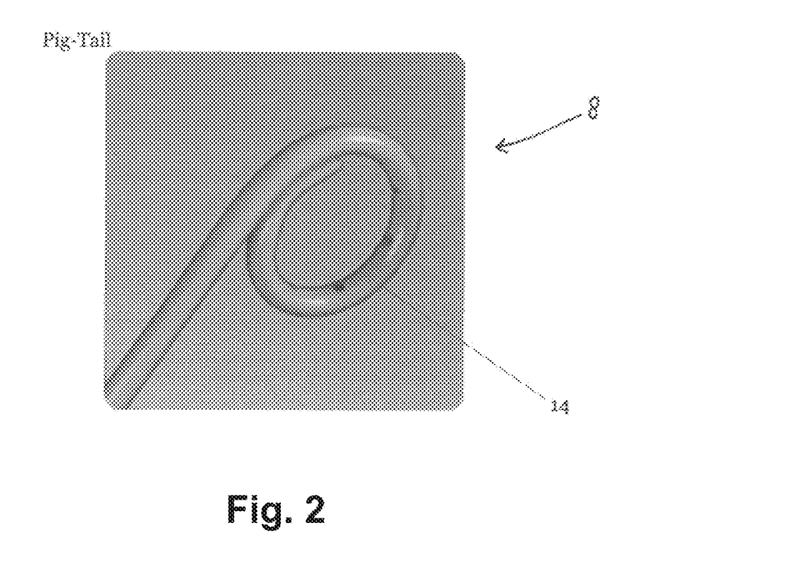
FIG. 2 shows a distal tip of the pig-tail configuration of the distal end of the catheter of FIG. 1.
Figure 3A:
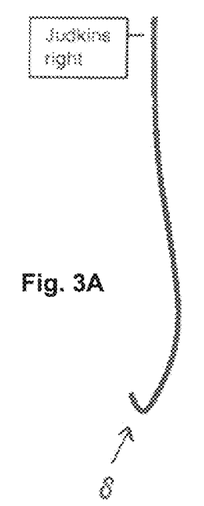
FIGS. 3A-D show alternative tips in accordance with alternative embodiments of the invention including Judkins right (FIG. 3A), Judkins left (FIG. 3B), Amplatz left (FIG. 3C), Hockey stick (FIG. 3D)
Figure 3B:
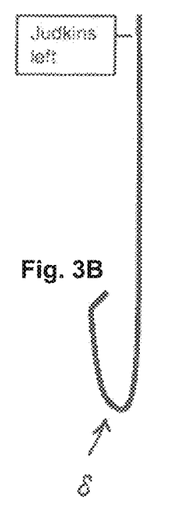
Figure 3C:
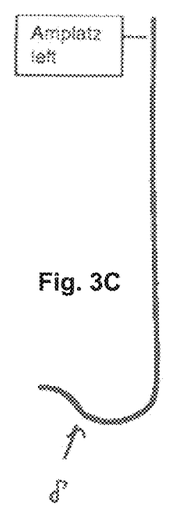
Figure 3D:
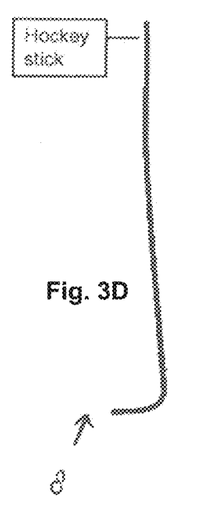
Figure 4:
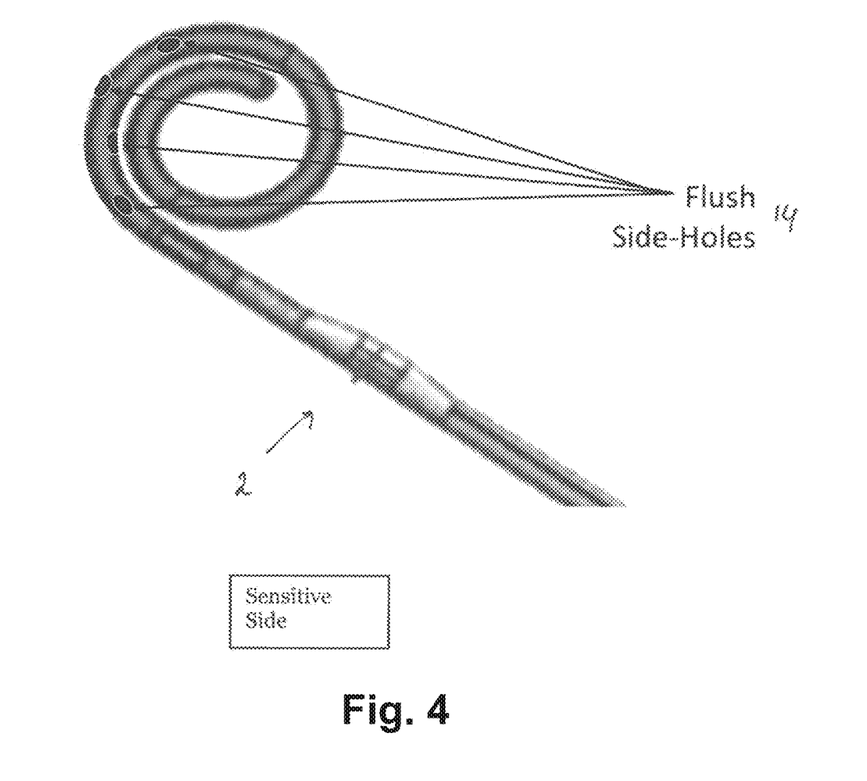
FIG. 4 shows al alternative embodiment of the invention with flush side-holes.
Figure 5:
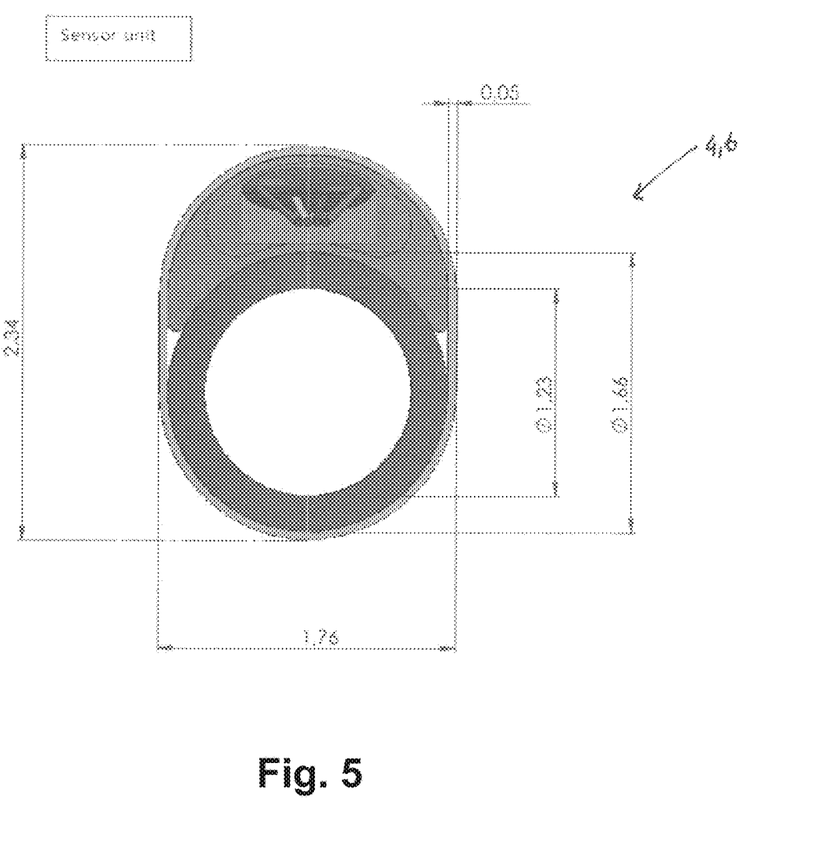
FIG. 5 shows a detail of the catheter of FIG. 1.
Figure 6:
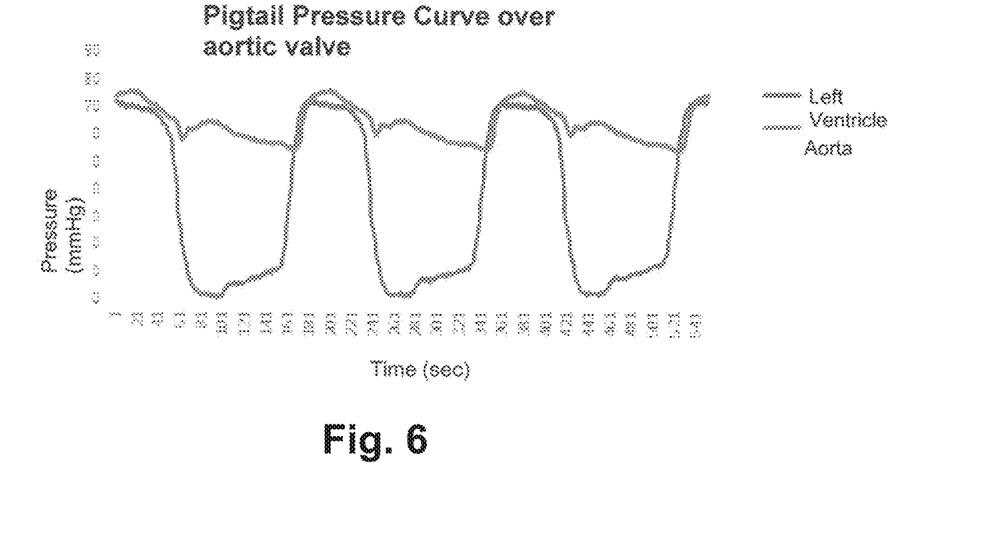
FIG. 6 shows a pigtail pressure curve over the aortic valve with the catheter of FIG. 1 when measuring the pressure in two locations simultaneously, the left ventricle (bottom curve) and the aorta (top curve)
Figure 7:
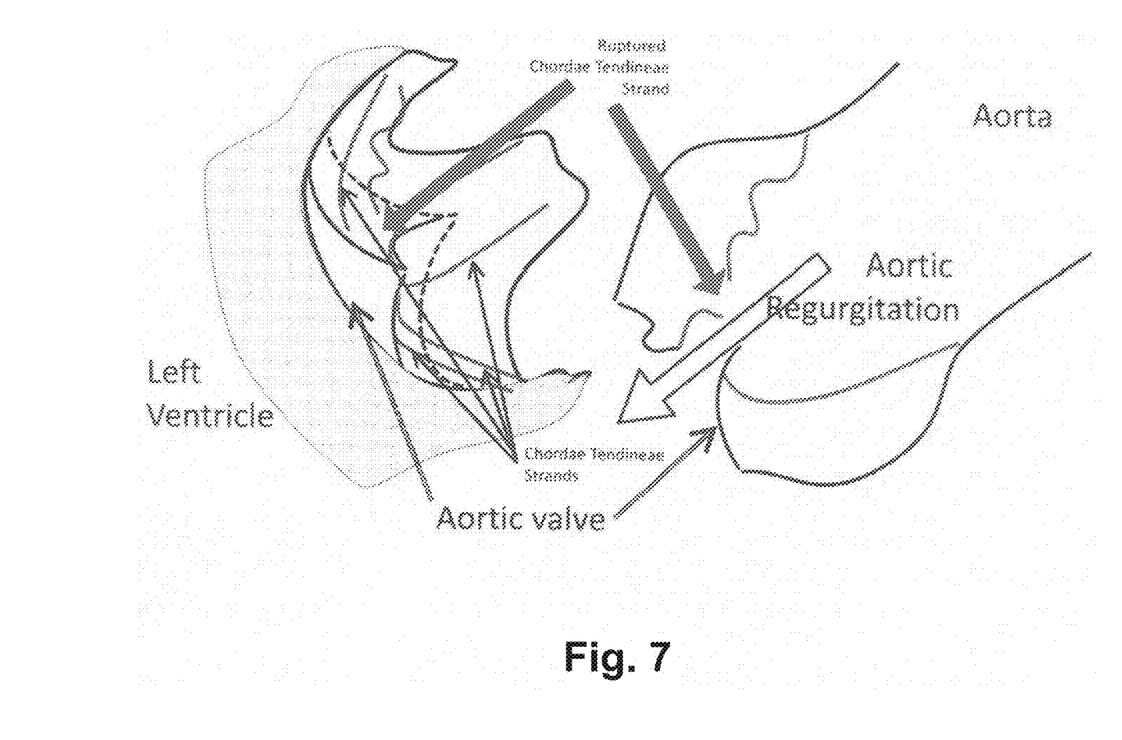
FIG. 7 shows the field for application of the catheter of FIGS. 1-5 with ruptured and unruptured Chordae Tendineae strands in relation to aortic regurgitation.
Figure 8A:
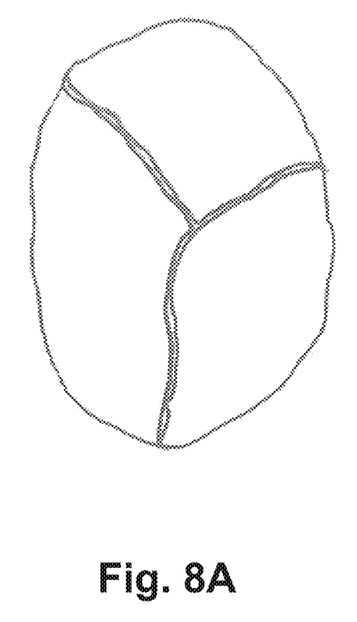
FIGS. 8A-B show a healthy aortic valve (FIG. 8A) and an aortic valve with unhealthy stenosis (FIG. 8B).
Figure 8B:
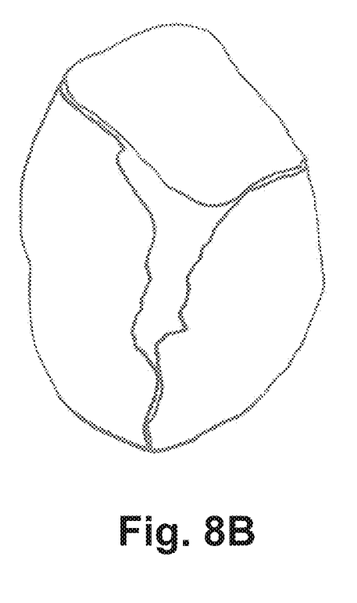

Catheter 2 (FIG. 1) comprises two (2) pressure sensors 4, 6. One sensor 4 at distal segment 8 of pigtail (sensor 1), one sensor 6 recessed on the main shaft 10 (sensor 2). A distal pressure chip 12 of sensor 4 is mounted on the exterior of the catheter shaft, facing outward. In use, the distal pressure sensor 4 measures the in-situ pressure under direct fluid contact with the lumen/reservoir. During clinical practice the distal pressure sensor 4 is generally placed inside the left ventricle. The second pressure sensor 6 is also placed on the exterior 10 of the shaft of catheter 2, proximal from first sensor 4. The second sensor 6 will be placed in the aorta on the outflow side of the aortic valve transition, originating in the left ventricle. The location for in-situ pressure measurement with respect to the second, proximal, pressure sensor 6 can, more specifically, be the aortic arch. The proximal pressure sensor 6 is facing outward, in direct fluid contact with the fluid-flow of the aorta. Flush side holes 14 are provided as can be seen in FIGS. 2 and 4.

In the illustrated embodiment catheter 2 shows wire 16, shrinking tube 18, basecoat 20, braid 22 and topcoat 24. Body 10 comprises angle α.

Catheter 2 in the illustrated embodiment comprises at least two sensors 4, 6, whereof:
a. Outside pressure sensor (sensor 1) 4 is used to measure in-situ ventricular pressure through direct fluid contact.
b. Outside pressure sensor (sensor 2) 6 is used to measure in-situ aortic pressure through direct fluid contact.

Lumina may be connected to the backside of the sensors, the side that is not exposed to the fluid in which the pressure is recorded. These lumina can act as a pressure vents, allowing for stabilization and real-time calibration of the pressure recordings. In this measurement configuration both pressure sensor chips act as differential pressure sensors and are therefore not sensitive to atmospheric changes or, in reference to other measurement designs (such as a hemodynamic system, operating by means of a fluid column, transferring the pressure over a distance to an external pressure sensor. The invention is as such not sensitive to the height of fluid columns in the patient's body, or respectively with respect to the connections on the proximal end of catheter 2 to pressure transducers as used in a conventional hemodynamic configuration, nor will the invention produce pressure values that are influenced by pressure build up internal to the measurement configuration, such as may result from temperature changes.

In the illustrated embodiment both pressure recordings are acquired simultaneously and synchronized in time, as well as synchronized with biological events, specifically cardiac contraction, next to potentially electrocardiogram (ECG) information obtained from electrodes, either placed on the surface of the skin of the patient undergoing diagnostic procedures or mounted on the catheter for in-situ depolarization recordings. Furthermore, pressure signal may additionally be synchronized with ElectroCardioGram (ECG) for determination of flow velocity based on wave-dispersion calculations with respect to the cardiac output fluid-dynamics. For the flow velocity determination, the acquisition of a high frequency-content pressure wave for each heart-beat is performed. For these purposes catheter 2 is capable of being functionally coupled to analysis system 102.

Referring to FIG. 1, an invention is presented that describes a system, means and methods for the minimally invasive detection of the pressure gradient across the aortic valve, and hence provide the ability to quantify the pathological condition with respect to the aortic valve. Recognized clinical parameters used for diagnostic analysis of the pathological condition of a patient's heart valve can be measured on a beat-by-beat basis, resolving the diastolic and systolic phases of the heart-beat, subsequently clinical prognoses parameters can be calculated such as the Regurgitation Index, Cardiac Output and Flow-Velocity, using documented analytical mathematical procedures. Referring to FIG. 1, an invention is presented that describes a system, means and methods for minimally invasive detection of the pressure gradient across a prosthetic valve, following either surgical intervention or transcatheter valve replacement, measuring the transient pressure behaviour in-situ in the first location and simultaneously and synchronized with this first recording measuring the transient pressure behaviour in the second location, as a function of time with respect to the cardiac motion.

In the current clinical procedures, the fluid pressure in different locations in the circulatory system of a patient as a function of time is most often determined by means of a fluid column connecting the orifice in the distal segment of a catheter body to a pressure sensor located in a detection system mounted on a pole standing beside the patient. In this situation the track of the fluid line leading to the sensor unit located on the exterior of the patient body has the potential of influencing the pressure magnitude due to movement of the fluid line, or the geometry of the path of the fluid-line, next to the respective height of attachment to the pressure sensor in relation to the anatomical position of the orifice used to acquire the localized pressure in the bloodstream. The fluid column has the potential for inertial dampening due to flow friction and the energy requirements to initiate the increase and decrease of flow velocity of a fluid column.

Next, some embodiments according to the invention will be briefly described. It will be understood that these embodiments are examples and other embodiments according to the invention can also be envisaged.

In Embodiment 1, the medical device having a construction of a minimum of two pressure sensor units, wherein the respective distal and proximal pressure sensors are spaced apart, placed on the exterior surface of a catheter body. The spacing is optimally configured to allow the measurement of a pressure gradient between the two pressure points that has minimal impact resulting from boundary flow conditions resulting from the geometry of the cardia and vascular system.

In Embodiment 2, the medical device comprises a minimum of one axial lumen running the length of the catheter.

In Embodiment 3, the device of Embodiment 1 is optionally configured to provide an outflow track on the distal end of the catheter body through a single lumen, or through a multitude of lumina.

In Embodiment 4, the device of Embodiment 1, 2 and 3 is optionally configured in a preform shape, resembling a Amplatz, PigTail, J-shape, Hockeystick, or shape combinations with respective straight segments in preferred locations.

In Embodiment 5, the device of Embodiment 1-4, respectively, has one or more radiopaque markers identifying the respective locations of the distal tip of the catheter as well as the individual locations of the various pressure sensors.

In Embodiment 6, the device of Embodiment 1-4, respectively, has a braided or reinforced catheter wall that supports the infusion of various liquids through one of the lumina of the catheter from the external proximal end, out of the distal tip. One of the fluids that can be injected can be a diagnostic fluid that provides an enhancement of visual contrast between the biological media in the volume of interest in the patient under radiographic examination. This injection may be achieved under elevated pressure, up to 1200 PSI, provided by specialized external injection equipment.

In Embodiment 7, the device of Embodiment 1-6 uses a bifurcation in the proximal configuration in order to separate the flush lumen from the venting lumen of the pressure sensors, next to feeding through of the electrical connections for the respective pressure sensor units.

Next, a more detailed description will be presented of Embodiment 1. It will be understood that this detailed description is merely exemplary in nature and is in no way intended to limit the invention, its application, or uses and/or may apply in similar manner to one or more of the other embodiments.

In Embodiment 1, the pressure detection units can operate under a multitude of sensing mechanism of action, wherein one option includes the uses of a piezo-resistive or MEMS detector either as a single unit operating in a Full-Bridge Wheatstone configuration, or respectively when a half-bridge or quarter bridge sensing design is used, compensated in a location more proximal from the sensor, acting to complete the full-bridge electronic configuration to providing built-in error detection and respective corrections to the acquired data stream with respect to, for instance, temperature effects; as well as measurement of temperature itself.

In Embodiment 1, the pressure detection units providing the means for corrections for changing boundary conditions to other pressure sensors on same catheter based on information from Full-Bridge Sentron pressure sensor In Embodiment 1, the pressure detection units can provide corrections for boundary conditions to other pressure sensors on other catheters placed in the same patient based on information from Full-Bridge Sentron pressure sensor; including a second transducer on other catheter placed in another vessel to measure regurgitation; yielding full identification of all vascular flow influences on clinical pathology.

In Embodiment 1, the pressure detection units supporting high data transfer rate, respectively: speed of data exchange, supporting frequency resolved data analysis well beyond (at least two orders of magnitude greater) the physiological changes with respect to time. The high frequency content of the acquired pressure signal evolution over time provides the means to calculate a rudimentary impression of the average flow rate in the circulatory system at the location between the sensors being addressed for pressure recordings, without the direct requirement of electronically coupling with the ECG data-stream.

In Embodiment 1, the pressure detection units operating under Low Power consumption requirements, since only one sensor is selected at a time. This can provide specific advantages when operating with the assistance portable data recorders which may be battery powered, and hence have operational time constraints.

The present invention is by no means limited to the above described preferred embodiments. The rights sought are defined by the following claims within the scope of which many modifications can be envisaged. For example, the present invention can be applied to alternative catheters 2 that is illustrated in FIG. 1.

The invention claimed is:

1. A blood pressure monitoring system comprising:
a catheter body; and
a construction having both distal and proximal pressure sensors that are spaced apart, and are placed on an exterior surface of a shaft of the catheter body, wherein each pressure sensor is not embedded in or disposed in a recess in the exterior surface of the shaft of the catheter body,
wherein the pressure sensors comprise connections that are configured such that in use the sensors can be connected to electronic sensor drivers and decoding and identification and signal processing devices, respectively individual or combined power sources connected to said electronic sensor drivers and said decoding and identification and signal processing devices, said electronic sensor drivers also connected to said identification and signal processing devices,
wherein each pressure sensor has a pressure sensing area facing radially outward such that the pressure sensing area is configured to be in use in direct contact with a local bloodstream in a cardiovascular circulatory system when the shaft of the catheter body including the pressure senors is in a blood vessel of the cardiovascular circulatory system such that the respective pressure sensors can measure a pressure in-situ on a first side of a lesion, stenosis, or orifice, and on a second side of the lesion, stenosis, or orifice,
wherein the pressure sensors in direct contact with the local bloodstream in the cardiovascular circulatory system when the shaft of the catheter body including the pressure sensors is in a blood vessel of the cardiovasular circulatory system and the pressure sensors are measuring the pressures on the first and second sides of the lesion, stenosis, or orifice the pressure sensors measurements will be unaffected by conditions resulting from urging diagnostic fluid through a single lumen, respectively any of multiple lumens of the catheter body up to 1200 PSI (approx. equivalence: 10345 kPa) pressure applied on a proximal entry of the catheter body, resulting in an outflow from a distal side of the catheter body.

2. The system of claim 1, wherein the pressure sensors are capable of operating under a data acquisition rate that is higher than a highest frequency information imbedded in a physiological process that is being monitored, and wherein said data acquisition processes is provided with adjustment means that are configured to be adjusted in operational frequency to suit an application and support energy consumption economy.

3. The system of claim 1, wherein the pressure sensors comprise one or more collectors configured for collecting pressure values based on a variety of technical mechanisms, including but not limited to: optical spectroscopic, respectively fiber-optic technology (e.g. laser-based fiber-Bragg grating); piezo-electric mechanism; capacitive sensing mechanism; cantilever mechanical technology; electromagnetic technology; resistive strain technology; thermal mechanism; ionization mechanism; acoustic, radio-frequency, respectively resonant or MEMS technology; or ISFET transistor junction electronic technology, hybrid sensor, and any combinations thereof.

4. The system of claim 1, wherein electronic values of a data acquisition can be routed to a signal processing and diagnostic value display system by means of signal pre-processing in a routing mechanism incorporated in an electronic plug and signal conditioning unit attached to the pressure sensors on the proximal end of the catheter body.

5. The system of claim 1, wherein the catheter body comprises a single lumen, or multiple lumina that are individually or combined encapsulated by a braided jacket material.

6. The system of claim 1, wherein the catheter body includes at least one side-hole in a distal segment of the catheter body and at least one hole in a distal tip orifice of the catheter body enabling outflow from a lumen of the catheter body.

7. The system of claim 1, wherein a distal segment of the catheter body having a shape of a "pig-tail" or J-shape (angiographic) catheter, having a shape of a left-, or respectively, right- "Amplatz" configuration, or Judkins coronary catheter, or other shaped tip configuration that is curved, is configured to be placed on a first side of a lesion.

8. The system of claim 1, wherein a distal segment of the catheter body includes mechanical attributes configured to anchor the distal segment of the catheter body on a first side of a lesion.

9. The system of claim 1, wherein a distal segment of the catheter body having a straight shape is configured to be placed on a first side of a lesion.

10. The system of claim 1, further comprising a bend on a distal segment of the catheter body configured for positioning the distal segment of the catheter body on a first side of a lesion.

11. The system of claim 1, wherein a pressure gradient between a first and second part of the catheter body across a lesion is measured.

12. The system of claim 1, wherein a frequency content of a pressure signal resulting from a heart beat is acquired and routed to a monitoring system connected to a proximal end of the catheter body.

13. The system of claim 1, wherein a spectral pressure wave is used to derive geometric information about the shape and surface contour of an enclosure on a first and respectively a second side of a lesion, and allows the information to contribute to a geometric analysis of the lesion between the first and second side.

14. The system of claim 1, wherein a first segment of the catheter body is curved or straight, a bend second, connecting with a second segment of the catheter body which is straight.

15. The system of claim 1, further comprising a section having a plurality of holes over a length between 1.5 to 2.5 cm in either a spiral configuration at incremental angular rotation of a single hole, respectively any combination of multiple holes in one circumferential placement; or an alternating configuration of two opposing holes at a fixed angle; or any other angular back-forth switching configuration.

16. The system of claim 1, further comprising a section having a plurality of holes over a length between 3.5 to 4.5 cm in either a spiral configuration at incremental angular rotation of a single hole, respectively any combination of multiple holes in one circumferential placement; or an alternating configuration of two opposing holes at a fixed angle; or any other angular back-forth switching configuration.

17. A method for measuring an in-situ blood-pressure difference between a left ventricular pouch and a volume in an aortic arch, comprising the step of providing and positioning a blood pressure monitoring system according to claim 1.

18. The system of claim 1, wherein the exterior surface of the shaft of the catheter body includes no device between the distal and proximal pressure sensors.

\* \* \* \* \*